(12) United States Patent
Gamba

(10) Patent No.: US 12,391,655 B1
(45) Date of Patent: Aug. 19, 2025

(54) MELAMINE PROCESS WITH A TWO-STAGE PURIFICATION OF MELAMINE OFFGAS

(71) Applicant: Casale SA, Lugano (CH)

(72) Inventor: Simone Gamba, Pagazzano (IT)

(73) Assignee: Casale SA, Lugano (CH)

( * ) Notice: Subject to any disclaimer, the term of this patent is extended or adjusted under 35 U.S.C. 154(b) by 0 days.

(21) Appl. No.: 18/710,989

(22) PCT Filed: Oct. 5, 2023

(86) PCT No.: PCT/EP2023/077650
§ 371 (c)(1),
(2) Date: May 16, 2024

(87) PCT Pub. No.: WO2024/074656
PCT Pub. Date: Apr. 11, 2024

(30) Foreign Application Priority Data

Oct. 7, 2022 (EP) .................................. 22200402
Feb. 23, 2023 (EP) .................................. 23158350

(51) Int. Cl.
*C07D 251/60* (2006.01)

(52) U.S. Cl.
CPC ............................ *C07D 251/60* (2013.01)

(58) Field of Classification Search
None
See application file for complete search history.

(56) References Cited

U.S. PATENT DOCUMENTS

| 4,455,423 | A | 6/1984 | Belot |
| 7,311,759 | B2 | 12/2007 | Schroder et al. |
| 2003/0028020 | A1 | 2/2003 | Gupta et al. |
| 2004/0073027 | A1 | 4/2004 | Coufal et al. |

FOREIGN PATENT DOCUMENTS

| EP | 2907567 A1 | 8/2015 |
| EP | 3053915 A1 | 8/2016 |
| EP | 3208264 A1 | 8/2017 |
| WO | 2024/083571 A1 | 4/2024 |

OTHER PUBLICATIONS

Written Opinion of the International Searching Authority issued Jan. 22, 2024 in connection with PCT/EP2023/07858.
Gamba Simone, Casale LEM Improved Process: Know-How and Technology, The Best Mix To Maximize Environmental Sustainability, Nitorgen + Syngas, Mar. 29, 2022, International Conference.
Drennan et al., "Urea Deposits: Risk Assessment or Direct Prediction?", Converge CFD Software, https://convergecfd.com/blog/urea-deposits-risk-assessment-or-direct-prediction, May 8, 2024, 1-8.
International Search Report issued Nov. 20, 2023 in connection with PCT Application No. PCT/EP2023/077650.
Written Opinion of the International Searching Authority issued Nov. 20, 2023 in connection with PCT Application No. PCT/EP2023/077650.

*Primary Examiner* — Paul V Ward
(74) *Attorney, Agent, or Firm* — Akerman LLP

(57) ABSTRACT

A process for the synthesis of melamine including the purification of the offgas released by the synthesis of melamine by means of a first purification stage followed by a second purification stage (7); in the first purification stage (6) the offgas (3) is contacted with urea melt from the second stage (7) and with a recirculated urea melt (8, 9) containing ammonia and melamine precursors (5); in the second purification stage (7) the offgas from the first stage is contacted with fresh urea melt (15); said recirculated urea melt is withdrawn from bottom of the first stage and cooled in a shell and tube heat exchanger (11) to a temperature of not less than 165° C. preferably in the range 165° C. to 245° C. prior to reintroduction in said first stage.

20 Claims, 1 Drawing Sheet

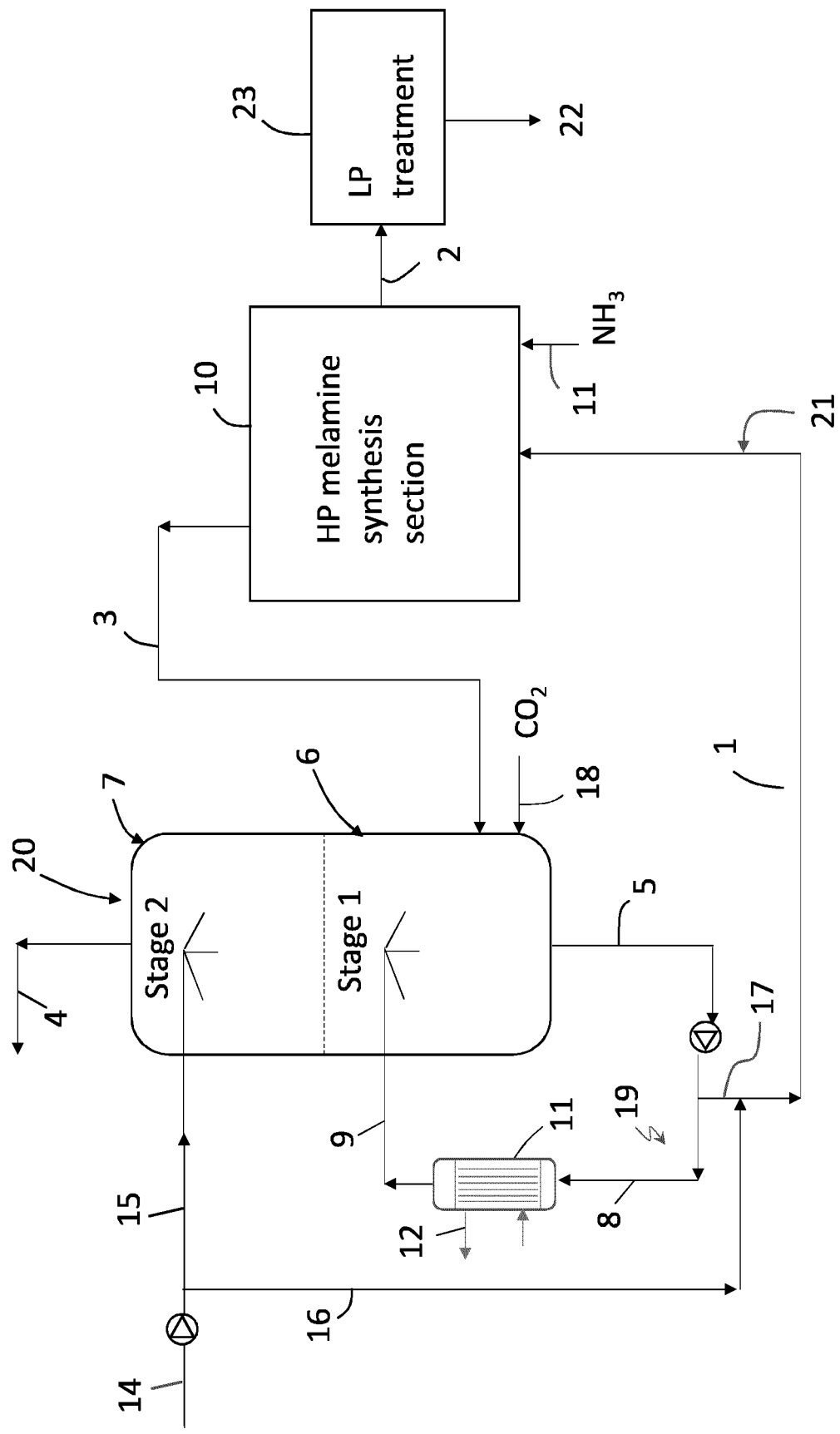

12,391,655 B1

MELAMINE PROCESS WITH A TWO-STAGE PURIFICATION OF MELAMINE OFFGAS

CROSS-REFERENCE TO RELATED APPLICATIONS

This application is a national phase of PCT/EP2023/077650, filed Oct. 5, 2023, and claims priority to EP 22200402.0, filed Oct. 7, 2022, and EP 23158350.1, filed Feb. 23, 2023, the entire contents of all of which are hereby incorporated by reference.

FIELD OF APPLICATION

The invention is in the field of industrial production of melamine. The invention particularly pertains to a high-pressure melamine synthesis process including a two-stage washing of the melamine offgas with urea melt.

PRIOR ART

Melamine is produced at an industrial scale starting from urea following either a non-catalytic high-pressure (HP) process or a low-pressure (LP) catalytic process. The non-catalytic high-pressure process is considered the most advantageous and is becoming predominant.

In the high-pressure process, a urea melt is reacted at pressure which is generally above 70 bar, typically 75 to 200 bar. The temperature of reaction is typically around 375° C.

The melamine synthesis section may include two reactors arranged in series wherein the first reactor produces a raw melamine melt and the second reactor removes carbon dioxide from the raw melamine melt using a stripping agent such as ammonia. Said second reactor may be termed post-reactor or stripping reactor. The first reactor and the second reactor may be separate vessels or combined in a single apparatus.

The melamine-containing product stream is sent to further treatments, typically in a plant section operating at a lower pressure than the pressure of the melamine synthesis section. Said treatments may include quenching, purification, crystallization, solid-liquid separation and drying, so that said product stream is converted into a solid melamine product of a desired purity. Typically, melamine purification and crystallization are carried out in an alkaline environment and ammonia or sodium hydroxide are the most commonly used alkaline agents.

Irrespective of the configuration of the synthesis section and of the section of the plant treating the raw melamine melt from the synthesis section itself, the reaction of urea to melamine produces a gaseous stream containing predominantly ammonia and carbon dioxide known as offgas, and further containing some melamine carried by the gas as well as other minor components.

Said offgas, which is liberated during the synthesis of melamine, is also termed "melamine offgas". Typically, the melamine offgas is recycled as a feed material for a tied-in urea plant. A combination of production of urea and melamine is attractive because urea is the reagent for the production of melamine and the offgas released during the synthesis of melamine contain ammonia and carbon dioxide which are the starting products for the urea synthesis. However, recycling the melamine offgas to a urea plant requires a proper purification and recover of melamine contained therein.

U.S. Pat. No. 7,311,759 discloses to purify the melamine offgas with a double-stage scrubbing process. The two scrubbing stages are arranged vertically, the second stage being above the first stage. The melamine offgas is supplied to the first stage and a urea melt is introduced from above into the second stage. The urea melt traverses the two stages in countercurrent with the offgas. The contact between the offgas and the falling urea melt generates melamine precursors such as ammeline and cyanuric acid. Accordingly, a urea melt containing ammonia and melamine precursors is withdrawn from the bottom of the scrubber and partially recirculated to the first stage. The recirculated portion of urea melt is cooled in a urea melt cooler prior to reintroduction into the first stage. Cooling the urea melt recovers the heat released by the scrubbing process, particularly by the absorption of the offgas in the urea melt.

The non-recirculated portion of urea melt containing the melamine precursors is sent to the melamine synthesis section. This provides an increase in the energy efficiency of the process because less energy is required for the formation of melamine starting from said precursors rather than from pure urea melt.

Therefore, the above-described double stage scrubbing process is attractive and improves the energy efficiency of the process; however, it still has a few disadvantages.

The melamine contained in the offgas fed to the scrubber can react with said precursors, especially with cyanuric acid, to generate melamine cyanurate. Melamine cyanurate has a low solubility in urea melt under the operating temperature of the scrubber and may precipitate as melamine cyanurate, particularly in the above-mentioned urea melt cooler of the recirculation line. Said precipitation may be detrimental to the operation of the cooler. Accumulation of the melamine cyanurate may obstruct the recirculation flow and reduce the heat exchange coefficient. The decrease of the heat transfer coefficient and/or of the recirculation flow may also increase the temperature of the urea melt in the cooler and, consequently, in the first stage, which increases the risk of corrosion in the heat exchanger or in the offgas scrubber, particularly at bottom of the scrubber. The above drawbacks may render the urea melt cooler unserviceable and cause a complete shutdown of the plant.

SUMMARY OF THE INVENTION

The invention aims to overcome the above drawbacks of the prior art. In particular the present invention aims to provide an optimized process for the synthesis of melamine, which is not subjected, or at least less sensitive, to the above drawbacks.

Accordingly, an aspect of the present invention is a process for the synthesis of melamine according to claim 1.

The process includes a two-stage purification of melamine offgas withdrawn from a melamine synthesis section. The purification process includes a first purification step performed in a first stage and a second purification step performed in a second stage. Said two steps are carried out in sequence, so that the partially purified offgas effluent from the first stage is processed in the second stage. The first purification step can be performed at a higher temperature than the second purification step, or the two steps may be performed substantially at the same temperature.

In the first purification stage, the melamine offgas is contacted (i.e., washed) with a urea melt which includes a recirculated urea melt containing ammonia and melamine precursors. Said recirculated urea melt is withdrawn from the first stage and reintroduced into the same first stage after cooling. In the second purification stage, the offgas effluent from the first stage is further contacted with a fresh urea melt.

The process of the invention is characterized in that said recirculated urea melt, prior to reintroduction into the first stage, is cooled in a shell and tube heat exchanger to a temperature equal to or above (that is, not less than) a minimum temperature of 165° C. In certain embodiments said minimum temperature may be 170° C. or 175° C. or 180° C. The temperature to which the recirculated urea melt is cooled is preferably in the range 165° C. to 245° C., more preferably 170° C. to 235° C. In certain embodiments, said temperature is in the range 175° C. to 225° C. or 180° C. to 220° C. Preferably said temperature is the temperature of the urea melt measured at the outlet of the heat exchanger.

In a preferred embodiment, the mass ratio between said recirculated urea melt and the solid melamine product of the melamine plant, wherein the two-stage purification of the offgas is operated, is between 11 and 30. In embodiments of the invention, said mass ratio may be 13 to 28 or 14 to 22.

Said solid melamine product is the solid melamine obtained after the treatment of the raw melamine melt at a pressure lower than the synthesis pressure, for example after quenching, purification, crystallization, separation of the so obtained crystals of melamine from the remaining liquor and drying of said crystals. The mass rate of said solid melamine product normally denotes the capacity of the plant.

The selected temperature of at least 165° C., preferably in the range 165° C. to 245° C., to which the recirculated urea melt is cooled prior to reintroduction in the first stage, prevents the precipitation of melamine cyanurate and corrosion issues. Particularly, keeping the recirculated urea melt above 165° C. avoids the precipitation of the cyanurate, whereas a temperature not greater than 245° C. is appropriate to avoid corrosion, i.e. to control the corrosive effect of the urea melt flowing through the urea melt cooler and added to the first stage. The applicant has found that the bottom of the offgas scrubber is particularly exposed to the risk of corrosion and, thanks to the present invention, this risk is reduced. Accordingly, the risk of unwanted shutdowns of the plant is reduced, the efficiency of the purification process can be maintained in the optimal range.

The above-mentioned mass ratio between the recirculated urea melt and the amount of solid melamine produced (melamine plant capacity) provides optimal contact between urea and melamine offgas relative to size of the apparatus and power required for pumping.

A further aspect of the invention is a combined process for production of urea and melamine according to the claims.

DESCRIPTION OF THE INVENTION

The invention concerns a process for the synthesis of melamine. A feed stream of urea melt is reacted under non-catalytic high pressure melamine synthesis conditions to generate a raw melamine product and a stream of melamine offgas comprising ammonia, carbon dioxide, melamine and minor components. The synthesis pressure is preferably 70 bar or above, for example 70 bar to 200 bar.

Said melamine offgas is subjected to a purification process, typically to allow recycling the offgas to a tied-in urea plant. The purification process is basically a washing process (also termed scrubbing process) with a urea melt. The offgas purification process is performed at a high pressure, preferably of at least 50 bar and more preferably equal to the melamine synthesis pressure.

The purification process includes a first purification step performed in a first purification stage and a second purification step performed in a second purification stage. Said purification steps are carried out in sequence so that the melamine offgas is subject to the first purification step and the so obtained partially purified gas is further processed in the second purification step. Said first purification step is performed at a higher temperature than the second purification step.

In the first stage, the melamine offgas is contacted with a urea melt which includes a recirculated urea melt taken from the first stage itself. The urea melt which contacts the offgas in the first stage may include a urea melt previously added in the second stage and said recirculated urea melt. Said recirculated urea melt contains ammonia and melamine precursors and is cooled before reintroduction in the first stage.

According to the invention said recirculated urea melt containing ammonia and melamine precursors is cooled in a shell and tube heat exchanger to a temperature of not less than 165° C. prior to re-introduction in the first purification stage.

Preferably the recirculated urea melt is cooled in the tube side of said heat exchanger and heat removed from the urea melt is used to produce steam in the shell side of said heat exchanger. The temperature of the steam produced in the shell side is preferably between 160° C. and 240° C., more preferably 165° C. to 230° C.

In some embodiments the recirculated urea melt is cooled in the above-mentioned heat exchanger to a temperature of not less than 170° C. or not less than 175° C. or not less than 180° C. Preferably said temperature is also not greater than 245° C. or not greater than 235° C. or not greater than 225° C. or not greater than 220° C. Said temperature is preferably 165 to 245° C. or 170 to 235° C. or 175 to 225° C. or 180 to 220° C. The lower limits and upper limits of the above-mentioned ranges may be combined. For example, further embodiments include that said temperature is 170 to 245° C. or 175 to 245° C. or 175 to 235° C. or 180 to 245° C. or 180 to 235° C.

Depending on the temperature to which the recirculated urea melt is cooled, the temperature of the steam produced in the heat exchanger may be 170 to 220° C. or 175 to 220° C. or 170 to 215° C. or 175 to 215° C.

Said temperature of the steam production in the shell side is selected to keep the inner surface of the tubes of the heat exchanger above the temperature at which precipitation of melamine cyanurate starts. The applicant has found that the inner surface of tubes, which is contact with the recirculated urea melt, is the point most exposed to the unwanted precipitation of melamine cyanurate. Furthermore, a melamine plant typically comprises a steam network at around 6 barg, which corresponds to 165° C., so that the production of steam in the urea melt cooler seamlessly integrates with the steam network of the melamine plant.

The applicant has found that cooling the urea melt to not less than 165° C. is advantageous contrary to the customary practice which prompts to cool said recirculated stream as much as possible insofar the urea is above its melting temperature, to recover heat and reduce the recirculated flow rate. The applicant has judiciously found that keeping the recirculated urea melt above 165° C. reduces the drawbacks connected to precipitation of melamine cyanurate in the urea melt cooler so that the apparent disadvantage in terms of increased recirculated flowrate is well compensated.

The temperature of the shell-side steam is also in contrast to the customary approach of heat exchanger design, which would prompt to produce steam at a temperature and pressure as low as possible, to increase the difference of temperature across the urea melt cooler and make said cooler smaller.

In the second stage, a fresh urea melt is introduced. The term fresh urea melt denotes for example the urea melt obtainable from a urea plant after recovery of unreacted matter and evaporation of water. Typically, the urea melt contains at least 96% urea, the balance being residual water and unavoidable impurities.

According to a preferred embodiment, the two purification stages work with a counter-current flow. In the second stage, the melamine offgas from the first stage is contacted counter-current with a fresh urea melt; in the first stage, the melamine offgas is contacted counter-current with the urea melt from the second stage and with the recirculated urea melt containing ammonia and melamine precursors.

A preferred embodiment is as follows. The second purification stage is placed above the first purification stage; the melamine offgas flows upward in the first stage and then in the second stage; a urea melt is sprayed over the offgas from top of the second stage and flows downward through the second stage and the first stage; a urea melt loaded with ammonia and melamine precursors is collected at the bottom of the first stage and a portion thereof is recirculated to the same first stage after cooling-. Accordingly the melamine offgas is scrubbed in counter-current firstly with the urea melt from the second stage and the urea melt recirculated in the first stage; then with the fresh urea melt introduced in the second stage.

Preferably said first purification step is carried out in the temperature range 170° C. to 250° C., more preferably in the temperature range 175° C. to 240° C. Said second purification step is carried out preferably in the temperature range 135° C. to 230° C. Preferably urea melt is withdrawn from the first purification stage at a temperature in the range 170° C. to 250° C.

The urea melt withdrawn from the first stage is a mixture of fresh urea melt from the second stage and urea melt recirculated to the first stage.

The non-recirculated portion of the urea melt collected from the first stage may be added with fresh urea melt to form the feed of the melamine synthesis section. According to an embodiment, the urea melt feed stream supplied to the high-pressure melamine synthesis section includes an amount of the urea melt which is supplied to the second purification stage and an amount of the urea melt containing ammonia and melamine precursors which is withdrawn from the first purification stage. A portion of the urea melt containing ammonia and melamine precursors withdrawn from the first purification stage is recycled to the first purification stage and another portion is conveyed to the high-pressure melamine synthesis section.

The first step of purification may be performed with addition of carbon dioxide in the first stage. In an embodiment, a carbon dioxide stream is added to the melamine offgas which is conveyed to the first purification stage. In another embodiment a carbon dioxide stream is introduced directly into the first purification stage.

According to a preferred embodiment, the synthesis of melamine includes a conversion step and a stripping step, wherein said conversion step includes reacting said urea melt feed stream under suitable melamine synthesis conditions to generate a raw melamine product, and said stripping step includes the stripping of said raw melamine product in the presence of gaseous ammonia, to remove carbon dioxide contained in the raw melamine.

The conversion of urea into melamine is performed in a melamine synthesis section. In some embodiments, said melamine synthesis section includes a single reactor, from which the raw melamine and the melamine offgas are withdrawn. In other embodiments, said melamine synthesis section includes a primary reactor where urea melt is reacted, followed by a secondary reactor where the melamine-containing effluent of the primary reactor is stripped with gaseous ammonia. In such embodiments, each of the primary reactor and the secondary reactor produce a respective stream of melamine offgas. Both melamine offgas streams are made predominantly of ammonia and carbon dioxide, although they may differ in composition.

The melamine offgas subject to scrubbing with urea melt, in accordance with embodiments the invention, may include only the melamine offgas stream from the primary reactor or both melamine offgas streams from the primary reactor and secondary reactor, possibly combined into a single stream. In a further embodiment, a combined reactor performs the function of the primary reactor and secondary reactor; to this purpose, said combined reactor includes a primary reaction stage and a secondary reaction stage.

According to an embodiment, the off-gas is introduced via an off-gas distributor above or below a liquid level of the urea melt containing ammonia and melamine precursors. A preferred embodiment of said offgas distributor is disclosed in U.S. Pat. No. 7,311,759.

According to another embodiment, the purification process is carried out in a scrubber and said urea melt, prior to be injected into the second stage, is divided into a plurality of sub-streams and introduced at multiple locations e.g. at multiple heights in the second stage of said scrubber.

In a combined urea-melamine embodiment, ammonia and carbon dioxide are reacted to form a urea solution in a urea synthesis section, the urea solution is processed in at least one recovery section to obtain a purified urea solution and water is removed from the solution to form a urea melt. Said urea melt is used in the above-described process for synthesis of melamine. The melamine offgas generated during the synthesis of melamine is recycled to the production of urea.

The melamine synthesis is performed at a synthesis pressure which is typically above 70 bar, such as 70 to 200 bar and preferably 75 to 200 bar. The purification of the melamine offgas is performed at a pressure up to the synthesis pressure, typically in the range 50 to 200 bar. Preferably, the purification of the melamine offgas is performed substantially at synthesis pressure. Particularly, the offgas purification process may be performed at a pressure slightly less than the melamine synthesis pressure, wherein the difference is not more than 20 bar or not more than 5 bar.

EXAMPLES

Table 1 summarizes several experimental tests with a different temperature of the recirculated urea melt after cooling, measured at the outlet of the heat exchanger. For each test the expected lifetime of the heat exchanger and the scrubber (bottom part) was estimated and the occurrence of melamine cyanurate precipitation in the heat exchanger was also identified.

In the experimental tests according to cases 1 to 3 and 5 to 7, wherein the temperature of the recirculated urea melt was within the range 165° C. to 245° C., no precipitation of melamine cyanurate occurred in the heat exchanger and an expected lifetime of the heat exchanger greater than 15 years was estimated. In the comparative test of case 4, wherein the temperature of the recirculated urea melt at the outlet of the heat exchanger was 158° C., fouling of the heat exchanger was clearly detected. The shell side steam temperature was higher than 160° C. in the cases 1 to 3 and 5 to 7 and lower than 160° C. in the comparative case 4.

The fresh urea inlet and the urea circulating in the first stage are given in terms of mass of urea per mass of solid melamine obtained in the process.

generate a raw melamine product 2 and melamine offgas 3. Said melamine offgas 3 contains carbon dioxide, ammonia, some residual melamine and other minor components. Ammonia 11 is injected in the synthesis section 10 to act as a stripping agent to remove carbon dioxide from the raw melamine.

The synthesis section 10 may comprise two separate reactors wherein in the first reactor raw melamine is syn-

TABLE 1

| | Case 1 | | Case 2 | | Case 3 | | Case 4 (comparative) | |
|---|---|---|---|---|---|---|---|---|
| Temperature [° C.] | Offgas | Urea | Offgas | Urea | Offgas | Urea | Offgas | Urea |
| Inlet | 370 | 150 | 370 | 150 | 370 | 150 | 370 | 150 |
| Transition first/second stage | 242 | 205 | 225 | 195 | 225 | 195 | 225 | 195 |
| Outlet | 205 | 242 | 195 | 225 | 195 | 225 | 195 | 225 |
| Specific heat for steam production [kJ/mol urea] | 24 | | 29 | | 29 | | 29 | |
| Content of melamine precursors and condensed melamine in the urea melt fed to the melamine reactor | 7% | | 6% | | 6% | | 6% | |
| Fresh urea inlet [$t_{UREA}/t_{MELAMINE}$] | 3.1 | | 3.1 | | 3.1 | | 3.1 | |
| Circulating urea in the first stage [$t_{UREA}/t_{MELAMINE}$] | 20.5 | | 20.5 | | 32.0 | | 8.0 | |
| Temperature of recirculated cooled urea melt [° C.] | 220 | | 199 | | 208 | | 158 | |
| Melamine removal from the offgas (efficiency) | 100% | | 100% | | 100% | | 95% | |
| Pumping energy ratio | 1.0 | | 1.0 | | 1.6 | | — | |
| Melamine cyanurate precipitation in the heat exchanger | No | | No | | No | | Yes | |
| Expected equipment lifetime (years) | 15-20 | | >=20 | | >=20 | | — | |

| | Case 5 | | Case 6 | | Case 7 | |
|---|---|---|---|---|---|---|
| Temperature [° C.] | Offgas | Urea | Offgas | Urea | Offgas | Urea |
| Inlet | 370 | 150 | 370 | 150 | 370 | 150 |
| Transition first/second stage | 205 | 183 | 225 | 195 | 205 | 183 |
| Outlet | 183 | 205 | 195 | 225 | 183 | 205 |
| Specific heat for steam production [kJ/mol urea] | 35 | | 29 | | 35 | |
| Content of melamine precursors and condensed melamine in the urea melt fed to the melamine reactor | 4.5% | | 6% | | 4.5% | |
| Fresh urea inlet [$t_{UREA}/t_{MELAMINE}$] | 3.1 | | 3.1 | | 3.1 | |
| Circulating urea in the first stage [$t_{UREA}/t_{MELAMINE}$] | 20.5 | | 14.0 | | 28.0 | |
| Temperature of recirculated cooled urea melt [° C.] | 173 | | 187 | | 182 | |
| Melamine removal from the offgas (efficiency) | 100% | | 100% | | 100% | |
| Pumping energy ratio | 1.0 | | 0.7 | | 1.4 | |
| Melamine cyanurate precipitation in the heat exchanger | No | | No | | No | |
| Expected equipment lifetime (years) | >=20 | | >=20 | | >=20 | |

DESCRIPTION OF THE FIGURES

FIG. 1 is a schematic representation of a melamine synthesis process according to an embodiment of the invention.

The FIGURE illustrates a high-pressure melamine synthesis section 10 and a melamine offgas purification section comprising a scrubber 20.

The high-pressure melamine synthesis section 10 is supplied with a urea melt feed stream 1 and gaseous ammonia 11.

In the melamine synthesis section 10 the urea feed stream 1 is reacted under high-pressure synthesis conditions to thesized and in the second reactor ammonia is used as a stripping agent to remove the carbon dioxide from the raw melamine. Alternatively, the synthesis of raw melamine and stripping with ammonia can be carried out in a single reactor. In a preferred embodiment, a single reactor has coaxial zones for synthesis and stripping. For example, the synthesis is carried out in a central zone of the reactor and stripping is carried out in an annular zone wrapped around said central zone.

The melamine offgas 3 is sent to a scrubber 20. Said scrubber 20 comprises a first stage 6 and a second stage 7. The first stage 6 is in fluid communication with the second stage 7 so that the melamine offgas 3 enters the first stage 6 and the partially purified offgas obtained from said first stage 6 are further treated in the second stage 7. Preferably, the second stage 7 is above the first stage 6 as illustrated.

The first stage 6 receives, in addition to the melamine offgas 3, a stream of gaseous carbon dioxide 18. The second stage 7 receives a fresh urea melt 15 which is a portion of a urea melt 14 coming from a tied-in urea plant (which is not shown in the FIGURE). Said urea melt 15 is distributed, for example sprayed, from top of the second stage 7.

The scrubber 20 is traversed in counter-current by the upward flowing offgas and downward by the flowing urea melt.

Effluents of the scrubber 20 are a purified offgas 4 and a urea melt 5 containing ammonia and melamine precursors. The purified offgas 4 is withdrawn from top of the second stage 7, whereas said urea melt 5 containing ammonia and melamine precursors is collected from bottom of the first stage 6. Once extracted, said urea melt 5 is separated into a first portion 8 and a second portion 17. The first portion 8 is recycled to the first purification stage 6 after cooling in a shell-and-tube heat exchanger 11. Particularly the urea melt is recirculated via a recirculation line 19 including said heat exchanger 11. The cooled urea melt 9 leaves the heat exchanger 11 at a temperature in the range 165° C. to 245° C.

The shell side of the heat exchanger 11 produces steam 12 with heat removed from the first portion of recirculated urea melt 8. Preferably the temperature of said steam 12 is between 160° C. and 240° C. Particularly preferably, said steam is saturated steam at least 6 barg.

The scrubber works as follows: in the first stage 6, the ascending stream of melamine offgas 3 is washed and purified by counter-current contact with the recirculated and cooled urea melt 9, which contains ammonia and melamine precursors, and with the urea melt 15 descending from the second stage 7. The carbon dioxide 18 injected into the first stage 6, promotes the formation of the melamine precursors contained in the urea melt 5. The purified offgas 4 emerging from the second stage 7 can be recycled to a urea plant not shown in the FIGURE, for example to the urea plant which produces the urea melt 14.

The second portion 17 of the urea melt 5, that is the portion which is not recirculated to the first purification stage 6, is mixed with an amount 16 of the urea melt 14 to form the urea melt feed stream 1.

The raw melamine melt 2 is processed in a low-pressure section 23 to obtain solid melamine 22 of a desired purity. Said section 23 preferably includes quenching, purification, crystallization, solid-liquid separation and drying.

What is claimed is:

1. A process for the synthesis of melamine including the steps of:
   reacting a feed stream of urea melt under non-catalytic high pressure melamine synthesis conditions to generate a raw melamine product and an offgas comprising ammonia and carbon dioxide,
   subjecting said offgas to a purification process by washing the offgas with urea melt, to obtain a purified offgas and a urea melt containing ammonia and melamine precursors, wherein the purification process includes a first purification step performed in a first purification stage and a second purification step performed in a second purification stage,
   wherein said purification steps are carried out in sequence so that the offgas from the melamine synthesis is subject to the first purification step and the so obtained partially purified gas is further processed in the second purification step,
   wherein:
   during said first purification step, the offgas is contacted with urea melt comprising a recirculated urea melt containing ammonia and melamine precursors, said recirculated urea melt being withdrawn from the first stage and reintroduced in the same first stage,
   wherein said recirculated urea melt, before being reintroduced in the first stage, is cooled in a shell and tube heat exchanger to a temperature not less than 165° C.

2. The process according to claim 1 wherein said temperature, to which the recirculated urea melt is cooled, is not less than 170° C. or not less than 175° C. or not less than 180° C.

3. The process according to claim 1, wherein said temperature, to which the recirculated urea melt is cooled, is in any one of the following ranges: 165° C. to 245° C. or 170° C. to 235° C. or 175° C. to 225° C. or 180° C. to 220° C.

4. The process according to claim 1, wherein said recirculated urea melt is cooled in the tube side of said heat exchanger and heat removed from said urea melt is used to produce steam in the shell side of said heat exchanger.

5. The process according to claim 4, wherein the temperature of said steam produced in said shell side of the heat exchanger (11) is between 160° C. to 240° C.

6. The process according to claim 1, wherein in the first purification stage, said offgas is contacted in counter-current direction with the urea melt comprising the recirculated urea melt loaded with ammonia and melamine precursors;
   afterward in the second stage, the offgas emerging form the first stage is contacted in counter-current with a fresh urea melt;
   said fresh urea melt is introduced in the second stage and traverses in sequence the second stage and the first stage.

7. The process according to claim 1, wherein urea melt withdrawn from said first purification stage has a temperature in the range 170° C. to 250° C.

8. The process according to claim 1, wherein said second purification step is carried out in the temperature range 135° C. to 230° C.

9. The process according to claim 1, wherein said raw melamine melt is processed further to obtain a solid melamine product and wherein the mass ratio between said recirculated urea melt and said solid melamine product is between 11 and 30 or in the range 13 to 28 or in the range 14 to 22.

10. The process according to claim 1, wherein said urea melt feed stream includes fresh urea melt and a portion of the urea melt containing ammonia and melamine precursors withdrawn from the first purification stage.

11. The process according to claim 1, wherein carbon dioxide is added to said offgas in said first purification stage.

12. The process according to claim 1, wherein the synthesis of melamine includes a conversion step and a stripping step, wherein in said conversion step said urea melt feed stream is reacted under high-pressure melamine synthesis conditions to generate a raw melamine product containing carbon dioxide and in said stripping step said raw melamine product containing carbon dioxide is stripped in presence of gaseous ammonia.

13. The process according to claim 12, wherein:
   the synthesis of melamine is performed in a synthesis section including a primary reactor followed by a secondary reactor, wherein said stripping step is performed in the secondary reactor, and the offgas subject to said purification process includes offgas withdrawn from the primary reactor only or the offgas subject to said purification process includes offgas withdrawn from the primary reactor and offgas withdrawn from the secondary reactor, or wherein the synthesis of melamine is performed in a synthesis section including a single reactor, and the offgas subject to said purification process is withdrawn from said single reactor.

14. The process according to claim 1, wherein the offgas is introduced via an offgas distributor above or below a liquid level of the urea melt containing ammonia and melamine precursors.

15. The process according to claim 1, wherein said purification process is carried out in a scrubber and a fresh urea melt, prior to be injected into the second stage, is divided into a plurality of sub-streams and introduced at multiple locations in the second stage of said scrubber.

16. A combined process for the synthesis of urea and melamine wherein:
   ammonia and carbon dioxide are reacted to form a urea solution in a urea synthesis section;
   said solution is processed in at least one recovery section to obtain a purified urea solution;
   water is removed from said solution to form a urea melt;
   said urea melt is used in a process for synthesis of melamine according to claim 1;
   melamine offgas generated during the synthesis of melamine are recycled to the production of urea.

17. The process according to claim 2, wherein said temperature, to which the recirculated urea melt is cooled, is not greater than 245° C. or not greater than 235° C. or not greater than 225° C. or not greater than 220° C.

18. The process according to claim 5, wherein the temperature of said steam produced in said shell side of the heat exchanger is between 165° C. to 230° C.

19. The process according to claim 18, wherein said steam is saturated steam at a pressure of least 6 barg.

20. The process according to claim 1, wherein urea melt withdrawn from said first purification stage has a temperature in the range 175° C. to 240° C.

* * * * *